US008211449B2

(12) United States Patent
Aust et al.

(10) Patent No.: US 8,211,449 B2
(45) Date of Patent: Jul. 3, 2012

(54) PHARMACEUTICALLY ELEGANT, TOPICAL ANHYDROUS AEROSOL FOAM

(75) Inventors: Duncan T. Aust, San Antonio, TX (US); David P. Jones, San Antonio, TX (US); Bhavesh P. Shah, San Antonio, TX (US)

(73) Assignee: DPT Laboratories, Ltd., San Antonio, TX (US)

( * ) Notice: Subject to any disclaimer, the term of this patent is extended or adjusted under 35 U.S.C. 154(b) by 1249 days.

(21) Appl. No.: 10/875,470

(22) Filed: Jun. 24, 2004

(65) Prior Publication Data

US 2005/0287081 A1  Dec. 29, 2005

(51) Int. Cl.
*A61K 9/12* (2006.01)
(52) U.S. Cl. .................. 424/400; 424/45; 514/945
(58) Field of Classification Search .................. None
See application file for complete search history.

(56) References Cited

U.S. PATENT DOCUMENTS

| | | | | |
|---|---|---|---|---|
| 3,770,648 A | 11/1973 | Mackles | | 516/11 |
| 3,912,665 A | 10/1975 | Spitzer et al. | | 521/98 |
| 3,929,985 A | 12/1975 | Webb, Jr. | | 424/45 |
| 3,949,096 A * | 4/1976 | Johnson et al. | | 426/302 |
| 4,488,564 A | 12/1984 | Grollier et al. | | 132/202 |
| 4,574,052 A | 3/1986 | Gupte et al. | | 510/120 |
| 4,639,367 A | 1/1987 | Mackles | | 424/45 |
| 4,752,465 A * | 6/1988 | Mackles | | 424/45 |
| 4,889,709 A | 12/1989 | Mackles et al. | | 424/45 |
| 4,981,677 A * | 1/1991 | Thau | | 424/45 |
| 5,077,053 A * | 12/1991 | Kuncewitch et al. | | 424/441 |
| 5,250,289 A | 10/1993 | Boothroyd et al. | | 424/59 |
| 5,254,334 A * | 10/1993 | Ramirez et al. | | 424/70.24 |
| 5,262,407 A | 11/1993 | Leveque et al. | | 514/159 |
| 5,286,475 A * | 2/1994 | Louvet et al. | | 424/45 |
| 5,296,021 A * | 3/1994 | Clapp et al. | | 106/2 |
| 5,322,683 A | 6/1994 | Mackles et al. | | |
| 5,357,636 A | 10/1994 | Dresdner, Jr. et al. | | 2/161.7 |
| 5,409,706 A | 4/1995 | Ramirez et al. | | 424/401 |
| 5,618,523 A | 4/1997 | Zysman et al. | | 424/70.1 |
| 5,679,324 A | 10/1997 | Lisboa et al. | | 424/45 |
| 5,716,611 A | 2/1998 | Oshlack et al. | | 424/78.25 |
| 5,733,558 A | 3/1998 | Breton et al. | | 424/401 |
| 5,830,449 A | 11/1998 | Afriat et al. | | |
| 5,833,960 A | 11/1998 | Gers-Barlag et al. | | 424/59 |
| 5,888,489 A | 3/1999 | von Mallek | | 424/70.19 |
| 5,959,127 A | 9/1999 | Semeria et al. | | |
| 5,972,310 A * | 10/1999 | Sachetto | | 424/45 |
| 6,001,376 A | 12/1999 | Mahieu et al. | | |
| 6,013,269 A | 1/2000 | El-Nokaly et al. | | 424/401 |
| 6,121,210 A | 9/2000 | Taylor | | 508/208 |
| 6,162,775 A | 12/2000 | Methmanus-Spaltro | | 510/130 |
| 6,180,159 B1 * | 1/2001 | Villagran et al. | | 426/590 |
| 6,258,374 B1 | 7/2001 | Friess et al. | | 424/436 |
| 6,287,580 B1 | 9/2001 | Gott et al. | | |
| 6,375,938 B1 | 4/2002 | Clothier, Jr. et al. | | |
| 6,479,060 B1 | 11/2002 | Jones et al. | | |
| 6,485,715 B1 | 11/2002 | Smith et al. | | |
| 6,503,517 B1 | 1/2003 | Mohammadi et al. | | |
| 6,524,594 B1 | 2/2003 | Santora et al. | | 424/401 |
| 6,536,629 B2 | 3/2003 | van der Heijden | | 222/190 |
| 6,544,530 B1 | 4/2003 | Friedman | | 424/400 |
| 6,555,099 B2 | 4/2003 | Guskey et al. | | |
| 6,610,315 B2 | 8/2003 | Scholz et al. | | |
| 6,620,773 B1 | 9/2003 | Stork et al. | | 510/130 |
| 6,627,178 B1 | 9/2003 | Cawthon | | 424/45 |
| 6,949,249 B2 | 9/2005 | Healy et al. | | 424/401 |
| 7,250,174 B2 | 7/2007 | Lee et al. | | 424/401 |
| 2002/0086039 A1 | 7/2002 | Lee et al. | | 424/401 |
| 2002/0098159 A1 | 7/2002 | Wei et al. | | |
| 2003/0059382 A1 | 3/2003 | Brandt et al. | | |
| 2003/0143278 A1 | 7/2003 | DiPiano et al. | | 424/489 |
| 2003/0180337 A1 | 9/2003 | Streicher et al. | | |
| 2003/0185865 A1 | 10/2003 | Jentzsch et al. | | |
| 2003/0185877 A1 * | 10/2003 | Betz et al. | | 424/442 |
| 2003/0211066 A1 | 11/2003 | Scholz et al. | | |
| 2003/0215405 A1 | 11/2003 | Parker et al. | | |
| 2003/0224025 A1 | 12/2003 | Gotsche et al. | | 424/401 |
| 2003/0235539 A1 | 12/2003 | Mongiat et al. | | |
| 2004/0005282 A1 | 1/2004 | Gaetani et al. | | |
| 2004/0018228 A1 | 1/2004 | Fischell et al. | | 31/785 |
| 2004/0076651 A1 | 4/2004 | Brocks et al. | | 424/401 |
| 2004/0197276 A1 | 10/2004 | Takase et al. | | 424/47 |
| 2004/0265240 A1 * | 12/2004 | Tamarkin et al. | | 424/45 |
| 2005/0031547 A1 * | 2/2005 | Tamarkin et al. | | 424/45 |
| 2005/0255063 A1 * | 11/2005 | Fenwick-Le Vine | | 424/63 |
| 2005/0281755 A1 | 12/2005 | Zarif et al. | | 424/47 |
| 2005/0281806 A1 | 12/2005 | Trumbore et al. | | 424/94.65 |
| 2006/0275218 A1 | 12/2006 | Tamarkin et al. | | 424/45 |
| 2007/0041910 A1 | 2/2007 | Pitre et al. | | 424/45 |

FOREIGN PATENT DOCUMENTS

| | | |
|---|---|---|
| DE | 10138495 | 2/2003 |
| GB | 2275419 | 8/1994 |
| WO | WO 91/11991 | 8/1991 |
| WO | WO 96/11665 | 4/1996 |
| WO | WO 96/19921 | 7/1996 |
| WO | WO 03/051294 | 6/2003 |
| WO | WO 2005/097068 | 10/2005 |

OTHER PUBLICATIONS

Office Communication, issued in European Patent Application No. 05821068.3, dated Apr. 9, 2009.
Office Communication, issued in Chinese Patent Application No. 2005-0021096, dated May 8, 2009.

* cited by examiner

*Primary Examiner* — David J Blanchard
*Assistant Examiner* — Barbara Frazier
(74) *Attorney, Agent, or Firm* — Fulbright & Jaworski L.L.P.

(57) ABSTRACT

A topical pharmaceutical aerosol foam containing liquid silicones to enhance cosmetic elegance. Although liquid silicones are inherent defoamers, a high quality, stable foam is produced.

10 Claims, No Drawings

PHARMACEUTICALLY ELEGANT, TOPICAL ANHYDROUS AEROSOL FOAM

FIELD OF THE INVENTION

This invention relates to topical pharmaceutical compositions.

BACKGROUND OF THE INVENTION

Topical pharmaceutical compositions are, of course, well known. They can be used as water proofing agents, sunscreens, skin conditioning agents, lip balms, wound dressings, hair pomades, etc. Regardless of the specific use, common to pharmaceutically satisfactory topical actives are that they must stay on the skin for a sufficient period of time to allow the active to perform; they must not irritate the skin; and, they must be perceived by the patient as pharmaceutically elegant or the patient will simply not use them. By "pharmaceutically elegant", as those skilled in the art know, one means the skin feel to the patient is good. It must not be too watery or too greasy. Some say it relates to the creaminess or lubricity properties as well as 'moisture retaining' properties.

There is a continual need for improvements in topical carrier systems, particularly for those that are lipophilic in nature, most of which are perceived by consumers as too waxy or too greasy when smeared on the skin. This invention relates to this need.

While aerosol delivery lipophilic systems have been used for topicals before, a problem with typical aerosol systems is to develop one that does not feel greasy and which is cosmetically superior. Known non-aerosol compositions which provide a nongreasy feel in topicals can include liquid silicones such as cyclomethicone, hexamethyldisiloxane, and dimethiconol. However, such liquid silicones are recognized in the art as defoaming agents. Defoaming agents are not something that one would want to add to a topical aerosol composition where foaming is an essential part of the delivery system since they act to defoam. Surprisingly, it has been found, however, that in the current invention, a topical aerosol foam composition has been created that does contain a large quantity of liquid silicones and yet it unexpectedly produces quality foam.

This invention offers a number of other benefits to the user which are also desirable objectives. The drug delivery system in the form of foam facilitates a novel, yet efficient mode of topical drug delivery system. It also facilitates continuous product output thereby adding ease of application. When dispensed in small quantity, the drug delivery system in the form of a foam can also cover a larger surface area of application while also facilitating better product application in areas where conventional topical products cannot be as effective. The drug delivery system in the form of foam also facilitates the use of a lower dosage which can minimize adverse reactions. The other crucial benefit is that this foam form of delivery system is devoid of any contact with air, light, or any other form of contamination as this is a completely sealed system throughout the life of the product. Thus, light and oxidation prone topical actives can be preserved effectively in the aerosol system. The anhydrous system of the carrier further extends the preservation of topical actives that are otherwise easily degraded by presence of a water base.

Accordingly, it is a primary object of the present invention to prepare a topical application or pharmaceutical composition which is of widespread applicability (i.e. useful with many drug actives) and which is at the same time perceived by the user as pharmaceutically elegant.

Another objective of the present invention is to achieve the primary object with a composition especially adapted for lipophilic compounds and which can provide effective delivery in the form of a foam.

A yet further objective is to provide a method of preparation of a topical application or pharmaceutical composition in the form of a foam that achieves each of the above objectives or attributes.

The method and manner of achieving each of the above objectives as well as other objectives of the invention, will become apparent from the following detailed description of the invention.

SUMMARY OF THE INVENTION

A topical pharmaceutical aerosol foam composition containing a lipophilic compound, a liquid silicone, a foaming agent, a propellant and a topical pharmaceutical active. The composition may also contain rheology modifiers that serve as foam stabilizers. The composition exhibits excellent emollient and rub-in characteristics. The composition when expelled from an aerosolized container produces surprisingly good quality foam from a composition consisting of large quantities of liquid silicones, which are normally inherently de-foamers.

DETAILED DESCRIPTION OF THE PREFERRED EMBODIMENT

For describing the compositions certain definitional terms are appropriate. "Pharmaceutically elegant" has been previously defined. The "pharmaceutical composition" as used throughout the present specification and the accompanying claims is to be understood as defining the compositions of which the individual components or ingredients are themselves pharmaceutically acceptable, e.g. that is they are topically acceptable actives. Put another way, they are either FDA approved or on the GRAS safe list. The term "topically active pharmaceutical" is intended to be non-limiting and includes those pharmaceutical active agents that are commonly applied topically such as waterproofing agents, skinbarrier agents, skin conditioning agents, solvents, bio-adhesives, acne actives, analgesics, anesthetics, anorectics, antihistamines, anti-inflammatory agents, antibiotics, antifungals, antivirals, antimicrobials, scabicides, pediculicides, antineoplastics, antiperspirants, antipruritics, antipsoriatics, antiseborrheics, astringents, biologically active proteins and peptides, burn actives, cauterizing agents, depigmenting agents, diaper rash agents, enzymes, hair growth actives, hemostatics, keratolytics, canker sore actives, cold sore actives, photosensitizing actives, steroids, sunburn actives, sunscreens, vaginal actives, wart actives, wound care actives; and retinol, retinoic acid and retinoic acid derivatives. These may also include prescription and over-the-counter (OTC) drug products. It is understood that this list is by way of example and not a limitation with respect to the active. The term "pharmaceutically-effective amount of a topically active pharmaceutical" is intended to mean that a sufficient amount of the topically active pharmaceutical is present in the composition to perform its intended purpose.

In the present invention, there are five essential ingredients. The first is a lipophilic compound or combinations of lipophilic compounds selected from the group, including but not limited to, petrolatum, mineral oil, vegetable oils, fatty acids, glycerides, medium chain triglycerides, or combinations thereof. The amount of lipophilic compound or combinations of lipophilic compounds is from about 1% to about 80% by weight of the total composition. Preferably, the amount of lipophilic compound or combinations of lipophilic compounds is from about 5% to about 65% by weight of the total composition. Various grades of Petrolatum exist, one of which is manufactured by Crompton under the grade Perfecta; a source of the medium chain triglycerides is Neobee® 1053 manufactured by Stepan; and a source of mineral oil is Kaydol White Mineral Oil manufactured by Crompton. An example of a medium chain triglyceride is caprylic/capric triglyceride.

The second essential ingredient is a liquid silicone or a combination of liquid silicones which are used to overcome the oily/greasy feel of the lipophilic compound during application to the skin and to provide good skin feel and rub in characteristics. The liquid silicone is selected from the group consisting of silicones, silicone derivatives, cyclomethicone, or combinations thereof. The amount of liquid silicone or combinations of liquid silicones is from about 1% to about 80% by weight of the total composition. Preferably, the amount of liquid silicone or combinations of liquid silicones is from about 5% to about 35% by weight of the total composition. Preferably, the liquid silicone used is Cyclomethicone, one source of which is ST-Cyclomethicone 5-NF manufactured by Dow Corning.

The third essential ingredient is a foaming agent, which is capable of foaming a product containing the above referenced liquid silicone. The foaming agent used is selected from the group consisting of mono, di, tri esters of Sorbitol and fatty acids. The foaming agent can be selected from the group consisting of sorbitan caprylate, sorbitan diisostearate, sorbitan dioleate, sorbitan isostearate, sorbitan laurate, sorbitan monooleate, sorbitan trioleate, sorbitan sesquioleate, and combinations thereof. The amount of foaming agent used is from about 0.5% to about 25% by weight of the total composition. Preferably, the amount of the foaming agent used is from about 3% to about 7% by weight of the total composition. The preferred foaming agent used is Sorbitan Monooleate one source of which is SPAN™ 80V Pharma manufactured by Uniqema.

The fourth essential ingredient is a pharmaceutically-effective amount of a topically active pharmaceutical, or in other words, the drug active. Suitable drug active categories have been previously listed. Some of these in specific can be Hydrocortisone, Zinc Oxide, Titanium Dioxide, Retinol, Bacitracin Zinc, Polymyxin B Sulfate, Neomycin Sulfate, Tretinoin, Salicylic Acid, Lidocaine, Tetracaine, Sodium Sulfacetamide, Boric acid, Ketoconazole, Tolnaftate, Tretinoin, Anthralin, Zinc Pyrithione, Menthol, Thymol, Desonide, Methyl Salicylate, Camphor, Clobetasol Propionate, Aluminum Sulfate, Trypsin, etc. Generally, the drug actives are present in amount from about 0.01% to about 40% weight of the total composition.

And finally, the fifth essential ingredient is a propellant, which is used to expel the composition from the aerosol container. The propellant is selected from the group consisting of hydrocarbons like Butane, Propane, Pentane, Isopentane, Isobutane or Mixtures thereof supplied by Aeropres under the Trade name of A-70 and hydroflourocarbons like DuPont's Dymel 236fa, which is 1,1,1,3,3,3 hexafluoropropane or Dymel 227ea/P which is 1,1,1,2,3,3,3 heptafluoropropane or the propellant of choice here being Dymel 134a/P which is 1,1,1,2 Tetrafluoroethane. The amount of propellant used ranges from about 1% to about 30% by weight of the total composition. Preferably, the amount of propellant used ranges from about 5% to 20% by weight of the total composition.

The composition may further contain rheology modifiers, which are capable of sustaining the foam. The rheology modifier if used may be selected from the group consisting of polyoxyl 40 hydrogenated castor oil, beeswax, paraffin wax, or combinations thereof. Sources of the Polyoxyl 40 Hydrogenated Castor oil are Lipocol HCO 40 manufactured by Lipo Chemicals or Cremophor RH-40 manufactured by BASF. A source of the Beeswax is White Wax SP422P NF manufactured by Strahl and Pitsch, and a source of the Paraffin wax is SP-674 manufactured by Strahl and Pitsch. The amount of rheology modifier used in the composition ranges from about 0.05% to about 15% by weight of the total composition. Preferably, the amount of rheology modifier used in the composition ranges from about 1% to about 5% by weight of the total composition.

Critical to the invention, therefore, is the combination of all five of the essential ingredients listed above to create the desired pharmaceutically elegant foam. When these are used in combination with the surfactant system herein specified, the dispensed foam is stabilized and of good quality in the presence of what would otherwise be defoamer, i.e., the silicones.

The following examples are offered to further illustrate, but not necessarily limit both the process and the composition of the present invention.

EXAMPLE 1

Vehicle

| Ingredient | % w/w |
| --- | --- |
| Caprylic/Capric Triglyceride | 20.00 |
| Mineral Oil | 8.00 |
| Cyclomethicone | 31.25 |
| Sorbitan Oleate | 5.00 |
| Polyoxyl 40 Hydrogenated Castor Oil | 4.00 |
| Petrolatum | 30.00 |
| Beeswax | 0.75 |
| Hydrogenated Castor Oil | 1.00 |

All ingredients are weighed in a vessel and it is heated to 70-75° C., and mixed well until uniform. It is then cooled to ambient and pressurized in an aerosol can with Hydroflourocarbon in the ratio: Base: 85%, Propellant: 15%.

EXAMPLE 2

Diaper Rash

| Ingredient | % w/w |
| --- | --- |
| Caprylic/Capric Triglyceride | 25.50 |
| Mineral Oil | 8.00 |
| Cyclomethicone | 20.00 |
| Beeswax | 1.50 |
| Sorbitan Monooleate | 4.50 |
| Hydrogenated Castor Oil | 0.50 |
| Zinc Oxide | 40.00 |

All ingredients are weighed in a vessel except the Zinc Oxide and it is heated to 70-75° C., and mixed well until uniform. It is then cooled to 45° C. and gradually added is dispersed Zinc Oxide, thus avoiding any lump formation. It is then cooled to ambient and pressurized in an aluminum aerosol can with Hydroflourocarbon in the ratio: Base: 80%, Propellant: 20%.

EXAMPLE 3

Antipuritic

| Ingredient | % w/w |
|---|---|
| Caprylic/Capric Triglyceride | 24.50 |
| Mineral Oil | 10.00 |
| Cyclomethicone | 32.00 |
| Beeswax | 1.50 |
| Sorbitan Monooleate | 6.00 |
| Petrolatum | 25.00 |
| Hydrocortisone | 1.00 |

All ingredients are weighed in a vessel except Hydrocortisone and it is heated to 70-75° C. and mixed well until uniform. It is then cooled to 35° C. and then gradually added and dispersed is the Hydrocortisone. It is then cooled to ambient and pressurized in an aluminum aerosol can with Hydrofluorocarbon in the ratio: Base: 90%, Propellant: 10%.

For each of examples 1-3 the product when tested for foaming characteristics produces an elegant skin feel product with good and stable foam characteristics and the delivery was deemed excellent.

From the above examples, it can be seen that the invention accomplishes at least all of its stated objectives.

What is claimed is:

1. An anhydrous, topical pharmaceutical aerosol foam composition, comprising in pharmaceutically-elegant and effective amounts:
   a lipophilic compound comprising petrolatum;
   cyclomethicone;
   3 to 7% by weight of the total composition of a foaming agent consisting of mono-, di-, or tri-esters of sorbitol or combinations thereof selected from the group consisting of sorbitan caprylate, sorbitan diisostearate, sorbitan dioleate, sorbitan isostearate, sorbitan laurate, sorbitan monooleate, sorbitan trioleate, sorbitan sesquioleate, and combinations thereof;
   a topically active pharmaceutical; and
   a propellant,
   wherein the composition is comprised in an aerosol container, and
   wherein the amount of cyclomethicone ranges from about 5% to about 35% by weight of the total anhydrous, topical pharmaceutical aerosol foam composition.

2. The composition of claim 1 wherein the foaming agent is sorbitan monooleate.

3. The composition of claim 1 further comprising a rheology modifier.

4. The composition of claim 3 wherein the rheology modifier is selected from the group consisting of polyoxyl 40 hydrogenated castor oil, beeswax, paraffin wax, and combinations thereof.

5. The composition of claim 1 wherein the topically active pharmaceutical is selected from the group consisting of acne actives, analgesics, anesthetics, anorectics, antihistamines, anti-inflammatory agents, antibiotics, antifungals, antivirals, antimicrobials, scabicides, pediculicides, antineoplastics, antiperspirants, antipruritics, antipsoriatics, antiseborrheics, astringents, biologically active proteins and peptides, burn actives, cauterizing agents, depigmenting agents, diaper rash agents, enzymes, hair growth actives, hemostatics, keratolytics, canker sore actives, cold sore actives, dental actives, saliva actives, photosensitizing actives, skin protectant/barrier agents, steroids, sunburn actives, sunscreens, vaginal actives, wart actives, wound care actives; and retinol, retinoic acid and retinoic acid derivatives.

6. The composition of claim 1 wherein the propellant is a hydrocarbon.

7. The composition of claim 1 wherein the propellant is a hydrofluorocarbon.

8. The composition of claim 6 wherein the hydrocarbon is selected from the group consisting of butane, isomers of butane, propane, isomers of propane, pentane, isomers of pentane, and combinations thereof.

9. The composition of claim 7 wherein the hydrofluorocarbon is selected from the group consisting of 1,1,1,2 tetrafluoroethane and 1,1,1,2,3,3,3 heptafluoropropane.

10. The composition of claim 1 wherein the amount of lipophilic compound ranges from about 1% to about 80% by weight of the total anhydrous, topical pharmaceutical aerosol foam composition.

* * * * *

UNITED STATES PATENT AND TRADEMARK OFFICE
CERTIFICATE OF CORRECTION

| | | |
|---|---|---|
| PATENT NO. | : 8,211,449 B2 | Page 1 of 1 |
| APPLICATION NO. | : 10/875470 | |
| DATED | : July 3, 2012 | |
| INVENTOR(S) | : Aust et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1253 days.

Signed and Sealed this
Twenty-fifth Day of September, 2012

David J. Kappos
*Director of the United States Patent and Trademark Office*